US008636735B2

(12) United States Patent
Scopton et al.

(10) Patent No.: US 8,636,735 B2
(45) Date of Patent: *Jan. 28, 2014

(54) MULTIFUNCTION MEDICAL DEVICE AND RELATED METHODS OF USE (75) Inventors: Paul Scopton, Winchester, MA (US); Thinh Nguyen, Medford, MA (US); Stephen J. Perry, Shirley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/532,909

(22) Filed: Jun. 26, 2012

(65) Prior Publication Data
US 2012/0271305 A1 Oct. 25, 2012

Related U.S. Application Data (63) Continuation of application No. 11/822,914, filed on Jul. 11, 2007, now Pat. No. 8,226,647.

(60) Provisional application No. 60/831,920, filed on Jul. 20, 2006.

(51) Int. Cl.
*A61B 18/18* (2006.01)
(52) U.S. Cl.
USPC ................................. 606/48; 606/45; 606/60
(58) Field of Classification Search
USPC ...................................................... 606/46, 48
See application file for complete search history.

(56) References Cited

U.S. PATENT DOCUMENTS

| 5,403,311 | A | 4/1995 | Abele et al. |
| 6,152,924 | A | 11/2000 | Parins |
| 6,193,715 | B1 | 2/2001 | Wrublewski et al. |
| 2003/0065326 | A1 | 4/2003 | Wellman et al. |
| 2003/0199869 | A1 | 10/2003 | Johnson et al. |
| 2006/0200123 | A1 | 9/2006 | Ryan |
| 2007/0265618 | A1 | 11/2007 | Long |

FOREIGN PATENT DOCUMENTS

| EP | 0 640 317 A1 | 3/1995 |
| WO | WO 98/34550 | 8/1998 |

OTHER PUBLICATIONS

Written Opinion and International Search Report for PCT/US2007/07225 dated Dec. 17, 2007.

*Primary Examiner* — Linda Dvorak
*Assistant Examiner* — Jaymi Della
(74) *Attorney, Agent, or Firm* — Bookoff McAndrews, PLLC (57) ABSTRACT An embodiment of the invention may include a medical device. The medical device may include a flexible tube, an elongate member configured to cut tissue and extend from the flexible tube, and a cauterizing member configured to cauterize tissue and to move relative to the elongate member and the flexible tube. The cauterizing member may substantially surround at least a portion of the elongate member.

19 Claims, 9 Drawing Sheets

MULTIFUNCTION MEDICAL DEVICE AND RELATED METHODS OF USE

CROSS-REFERENCE TO RELATED APPLICATIONS

This application is a continuation of U.S. application Ser. No. 11/822,914, filed Jul. 11, 2007, now U.S. Pat. No. 8,226,647 B2, which claims the benefits of priority under 35 U.S.C. §119(e) to U.S. Provisional Patent Application No. 60/831,920, filed Jul. 20, 2006, for MULTIFUNCTION MEDICAL DEVICE AND RELATED METHODS OF USE, all of which are incorporated herein by reference.

DESCRIPTION OF THE INVENTION

1. Field of the Invention

A combined electro-cautery and electro-cutting device to be used in medical procedures, and related methods of use.

2. Background of the Invention

Cancerous or benign lesions of the gastrointestinal tract often start in the mucosal layer of the stomach or intestines. With improved diagnostics and screening, such lesions are being identified prior to extension into the wall of the stomach or intestines. Removal of such cancerous or benign lesions is desirable, preferably before their extension into the wall of the stomach or intestines.

One method of removing such lesions includes an invasive surgical resection of the lesion and the adjacent bowel. However, surgical approaches may cause trauma to the patient.

Another method of removing such lesions includes local excision of the mucosal, for example, with access via natural orifices. A variety of endoscopic instruments may be used in such a procedure.

One such instrument and method may include placing a chamber attached to the end of an endoscope near a lesion, applying suction to the lesion so as to draw the lesion in the chamber, and then using an electrosurgical snare within the chamber to excise the portion of the lesion disposed in the chamber. This may be done repeatedly to completely resect the affected tissue.

Another such instrument and method may include advancing a grasper to a lesion via a channel of an endoscope. The grasper lifts the lesion, and then an electrosurgical snare is passed through another channel of the endoscope. The electrosurgical snare is placed around the shaft of the grasper and is advanced to encircle the lifted tissue. The snare is then activated to excise the tissue.

Several other endoscopic instruments may be used in conjunction with one or more of the above-referenced methods. For example, a needle may be used to inject saline or other solution under the mucosal to raise the lesion away from the underlying muscle wall so as to limit perforation.

Current upper gastrointestinal (UGI) endoscopic mucosal resection (EMR) procedures may utilize one or more endoscopic instruments in one or more steps of the following sequence. First, a dye applicator may be used to identify suspect tissue. Cautery may then be used to mark the lesion margins. Injection, as described above, may be used to raise the mucosal tissue layer, followed by excision to remove the lesion, according to one of the above described methods, for example. A cautery may then be used to control bleeding due to the excised tissue. Irrigation may be used to cleanse the area where the lesion was excised. These endoscopic instruments and steps may be used on multiple, time-consuming occasions in a single resection procedure, which may require inserting and removing each of these instruments on multiple, time-consuming occasions.

SUMMARY OF THE INVENTION

In accordance with the invention, an embodiment of the invention may include a medical device. The medical device may include a flexible tube, an elongate member configured to cut tissue and extend from the flexible tube, and a cauterizing member configured to cauterize tissue and to move relative to the elongate member and the flexible tube. The cauterizing member may substantially surround at least a portion of the elongate member.

Various embodiments of the invention may include one or more of the following aspects: the cauterizing member may be configured to move longitudinally relative to the elongate member and the flexible tube; the elongate member may be configured to remain substantially stationary in a longitudinal direction relative to the flexible tube; a handle may include a first portion and a second portion; an elongate connector connecting the cauterizing member to one of the first portion and the second portion; movement of the first portion relative to the second portion may move the cauterizing member relative to the elongate member and the flexible tube; a cap connecting the elongate member to the flexible tube; the cap may define a first lumen configured to accommodate the elongate connector therethrough; the cap and the elongate connector may be configured to cooperate so as to substantially prevent fluid flow through the first lumen of the cap; the elongate connector may be configured to conduct current; the elongate connector may be configured to be electrically connected to both of the cauterizing member and the elongate member; at least one configuration the cauterizing member may be substantially surrounded by the flexible tube; a handle may include an electrical connector and a fluid connector; the elongate member may include a lumen; the electrical connector may be configured to be connected to a source of current and may be configured to be electrically connected to both of the cauterizing member and the elongate member; and the fluid connector may be configured to be connected to a source of fluid so as to provide fluid to the lumen of the elongate member.

Another embodiment of the invention may include a medical device. The medical device may include a flexible tube, an elongate member configured to cut tissue, a cauterizing member configured to move relative to the elongate member and the flexible tube, a handle configured to move relative to the elongate member and the flexible tube, and an electrical connector extending through the flexible tube and configured to move substantially synchronously with the cauterizing member and the handle relative to the elongate member and the flexible tube. The electrical connector may be configured to provide current to at least one of the elongate member and the cauterizing member.

Various embodiments of the invention may include one or more of the following aspects: the cauterizing member may substantially surround at least a portion of the elongate member; the elongate member may be configured to remain substantially stationary in a longitudinal direction relative to the flexible tube; the handle may include a first portion and a second portion; movement of the first portion relative to the second portion may move the cauterizing member relative to the elongate member and the flexible tube; the electrical connector may connect the cauterizing member to one of the first portion and the second portion; a cap may connect the elongate member to the flexible tube; the cap may define a lumen configured to accommodate the electrical connector therethrough; the cap and the electrical connector may be configured to cooperate so as to substantially prevent fluid flow through the lumen of the cap; in at least one configuration the cauterizing member may be substantially surrounded by the flexible tube; the handle may include the electrical connector and a fluid connector; the elongate member may include a lumen; the electrical connector may be configured to be connected to a source of current and may be configured to be electrically connected to both of the cauterizing member and the elongate member; the fluid connector may be configured to be connected to a source of fluid so as to provide fluid to the lumen of the elongate member; and the electrical connector may be configured to accommodate current flow to only one of the elongate member and the cauterizing member at any point in time.

A further embodiment of the invention may include a medical device. The medical device may include a flexible tube defining a lumen, an elongate member configured to cut tissue, the elongate member defining a lumen configured to accommodate fluid flow from the lumen of the flexible tube, a cauterizing member configured to move relative to the elongate member and the flexible tube; and an electrical connector disposed in the lumen of the flexible tube. The electrical connector may be configured to accommodate current flow to at least one of the elongate member and the cauterizing member when the electrical connector may be in contact with fluid disposed in the lumen of the flexible tube. The electrical connector may consist of an electrically conductive material.

Various embodiments of the invention may include one or more of the following aspects: the cauterizing member may be configured to move longitudinally relative to the elongate member and the flexible tube; the elongate member may be configured to remain substantially stationary in a longitudinal direction relative to the flexible tube; a handle may include a first portion and a second portion; movement of the first portion relative to the second portion may move the cauterizing member relative to the elongate member and the flexible tube; the electrical connector may connect the cauterizing member to one of the first portion and the second portion; a cap may connect the elongate member to the flexible tube; the cap may define a lumen configured to accommodate the elongate connector therethrough; the cap and elongate connector may be configured to cooperate so as to substantially prevent fluid flow through the lumen of the cap; the electrical connector may be configured to be electrically connected to both of the cauterizing member and the elongate member; in at least one configuration the cauterizing member may be substantially surrounded by the flexible tube; a handle may include the electrical connector and a fluid connector; the electrical connector may be configured to be connected to a source of current; and the fluid connector may be configured to be connected to a source of fluid so as to provide fluid to the lumen of the elongate member and the lumen of the flexible tube.

Yet another embodiment of the invention may include a method of treating tissue. The method may include providing a device including, a flexible tube, an elongate member configured to cut tissue, and a cauterizing member configured to move to a first position and a second position relative to the elongate member and the flexible tube. The first position may be different from the second position. The method may include positioning the cauterizing member in the first position such that the cauterizing member does not surround a portion of the elongate member, with the cauterizing member in the first position, cutting tissue via the portion of the elongate member, positioning the cauterizing member to the second position so as to substantially surround the portion of the elongate member, and with the cauterizing member in the second position, cauterizing tissue via the cauterizing member.

Various embodiments of the invention may include one or more of the following aspects: longitudinally moving the cauterizing member relative to the flexible tube; the device may further comprise a handle including a first portion and a second portion and an electrical connector connecting the cauterizing member to one of the first portion and the second portion; moving the first portion relative to the second portion so as to implement the positioning steps; moving the electrical connector via the movement of the first portion relative to the second portion; providing current to one of the cauterizing member and the elongate member via the electrical connector; surrounding the cauterizing member with the flexible tube during the cutting step; the elongate member may include a lumen; the device may further comprise a handle including an electrical connector and a fluid connector; the method may further comprise providing a source of current and a source of fluid; connecting the fluid connector to the source of fluid so as to provide fluid to the lumen; irrigating tissue via fluid flowing from the lumen; connecting the electrical connector to the source of current so as to provide a current to at least one of the cauterizing member and elongate member; and the elongate member may be configured to be substantially stationary relative to the flexible tube.

A yet further embodiment of the invention includes a method of treating tissue. The method may include providing a device including a flexible tube, an elongate member configured to cut tissue, a cauterizing member configured to move relative to the elongate member and the flexible tube, a handle portion configured to move relative to the elongate member and the flexible tube, and an electrical connector configured to move substantially synchronously with the cauterizing member and the handle portion relative to the elongate member and the flexible tube. The method may further include manipulating the handle portion so as to move the electrical connector and the cauterizing member relative to the elongate member and the flexible tube, providing current to the elongate member via the electrical connector, and providing current to the cauterizing member via the electrical connector.

Various embodiments of the invention may include one or more of the following aspects: positioning the cauterizing member such that the cauterizing member does not surround a portion of the elongate member and cutting tissue via the portion of the elongate member; positioning the cauterizing member so as to substantially surround the portion of the elongate member and cauterizing tissue via the cauterizing member; longitudinally moving the cauterizing member relative to the flexible tube; the device may further comprise a handle including the handle portion and a second portion; moving the handle portion relative to the second portion so as to implement the positioning steps; surrounding the cauterizing member with the flexible tube during the cutting step; the device may further comprise a handle including the handle portion, the electrical connector, and a fluid connector; the elongate member may include a lumen; providing a source of current and a source of fluid; connecting the fluid connector to the source of fluid so as to provide fluid to the lumen; irrigating tissue via fluid flowing from the lumen; connecting the electrical connector to the source of current so as to provide a current to at least one of the cauterizing member and elongate member; and the elongate member may be configured to be substantially stationary relative to the flexible tube.

Still another embodiment of the invention may include a method of treating tissue. The method may include providing a device including a flexible tube defining a lumen, an elongate member configured to cut tissue, the elongate member defining a lumen configured to accommodate fluid flow from the lumen of the flexible tube, a cauterizing member configured to move relative to the elongate member and the flexible tube, and an electrical connector disposed in the lumen of the flexible tube, the electrical connector being in electrical connection with both the elongate member and the cauterizing member, wherein the electrical connector consists of an electrically conductive material. The method may further include flowing fluid through the lumen of at least one of the flexible tube and the elongate member and providing current to at least one of the elongate member and the cauterizing member via the electrical connector while fluid may be disposed in the lumen of the flexible tube and may be in contact with the electrical connector.

Various embodiments of the invention may include one or more of the following aspects: positioning the cauterizing member such that the cauterizing member does not surround a portion of the elongate member and cutting tissue via the portion of the elongate member; positioning the cauterizing member so as to substantially surround the portion of the elongate member and cauterizing tissue via the cauterizing member; longitudinally moving the cauterizing member relative to the flexible tube; the device may further comprise a handle including a first portion and a second portion; the electrical connector may connect the cauterizing member to one of the first portion and the second portion; moving the first portion relative to the second portion so as to implement the positioning steps; moving the electrical connector via the movement of the first portion relative to the second portion; surrounding the cauterizing member with the flexible tube during the cutting step; the device may further comprise a handle including the electrical connector and a fluid connector; providing a source of current and a source of fluid; connecting the fluid connector to the source of fluid so as to provide fluid to the lumen of the elongate member; irrigating tissue via fluid flowing from the lumen of the elongate member; connecting the electrical connector to the source of current so as to provide a current to the at least one of the cauterizing member and elongate member; and the elongate member may be configured to be substantially stationary relative to the flexible tube.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to the present exemplary embodiments of the invention illustrated in the accompanying drawings. Wherever possible, the same reference numbers will be used throughout the drawings to refer to the same or like parts.

FIGS. 1, 1A-1D, 2, 2A, 3, and 3A-3B depict an exemplary embodiment of a medical device 1. Medical device 1 may be configured to combine excision, cautery, and irrigation features into a single device. Medical device 1 may have the advantage of permitting all three procedures to be conducted without using multiple instruments and any associated problems that come with using multiple instruments, including device exchange, additional time for the procedure, additional trauma to the patient, and increased cost.

Figures 2, 2A:
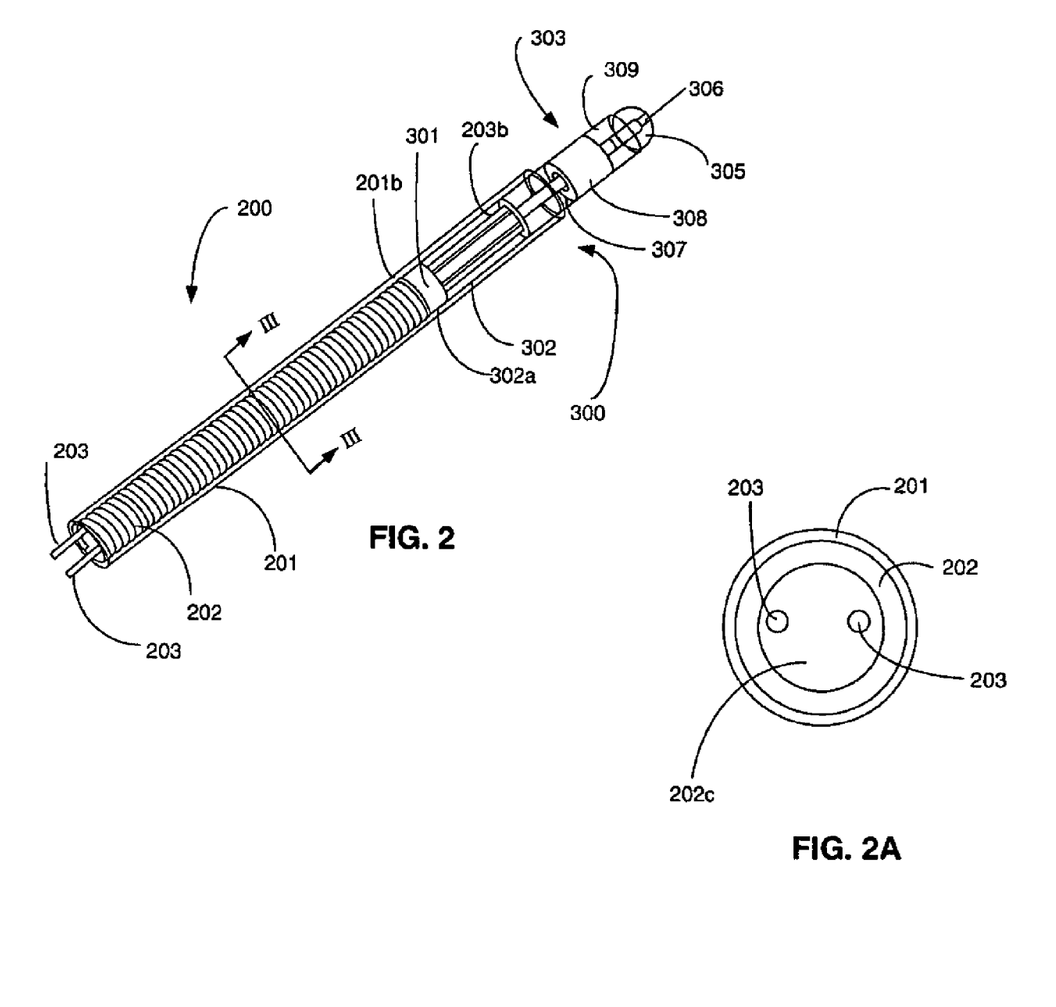
FIG. 2 is a perspective view of a medial portion and a distal portion of the medical device of FIG. 1 in a first configuration.
FIG. 2A is a cross-sectional view of a part of the medial portion along line III-III of FIG. 2.

Medical device 1 may include a proximal portion 100, a medial portion 200, and a distal portion 300. The major components of the proximal portion 100 may include a handle 101, an actuator 102 movable relative to handle 101, an electrical connector 103 connected to actuator 102, and an irrigation port 104 connected to handle 101. As shown in FIG. 2, for example, medial portion 200 may include, as its major components, an outer elongate member 201 or sheath, a middle elongate member 202 or coil, and elongate wire connectors 203. Elongate connectors 203 may connect to actuator 102 and electrical connector 103. A lumen 202c of middle elongate member 202 may be in fluid communication with port 104.

The major components of distal portion 300 may include a cap 301, a sheath 302, a capsule 303, an elongated member or knife 304 and a tip 305 with an orifice 306. Cap 301 may be disposed on an end of middle elongate member 202, and sheath 302 may be an extension of outer elongate member 201. Capsule 303, which performs cautery, and knife 304, which excises tissue, may have power supplied to them by elongate connectors 203. In this embodiment, a monopolar current may be provided to device 1.

Capsule 303 may move relative to cap 301, sheath 302, and knife 304, such that in a first configuration, a distal portion of knife 304 may be covered by capsule 303, and in a second configuration, the distal portion of knife 304 may be exposed to perform excisions. Orifice 306 and a lumen 310 of knife 304 may be in fluid communication with lumen 202c of middle elongate member 202 for the supply of irrigation fluid.

Tip 305 may be at a distal end of knife 304 to minimize perforation and assist in lifting target tissue for excision. Each of the various components of device 1, and their interconnection and function, will now be described in more detail.

FIGS. 2, 3, and 3A-3B depict an exemplary embodiment of distal portion 300. Distal portion 300 may include various components to perform excision, cautery, and irrigation. As mentioned above, distal portion 300 may include cap 301, sheath 302, capsule 303, knife 304, and tip 305 with orifice 306.

Figures 3, 3A, 3B:
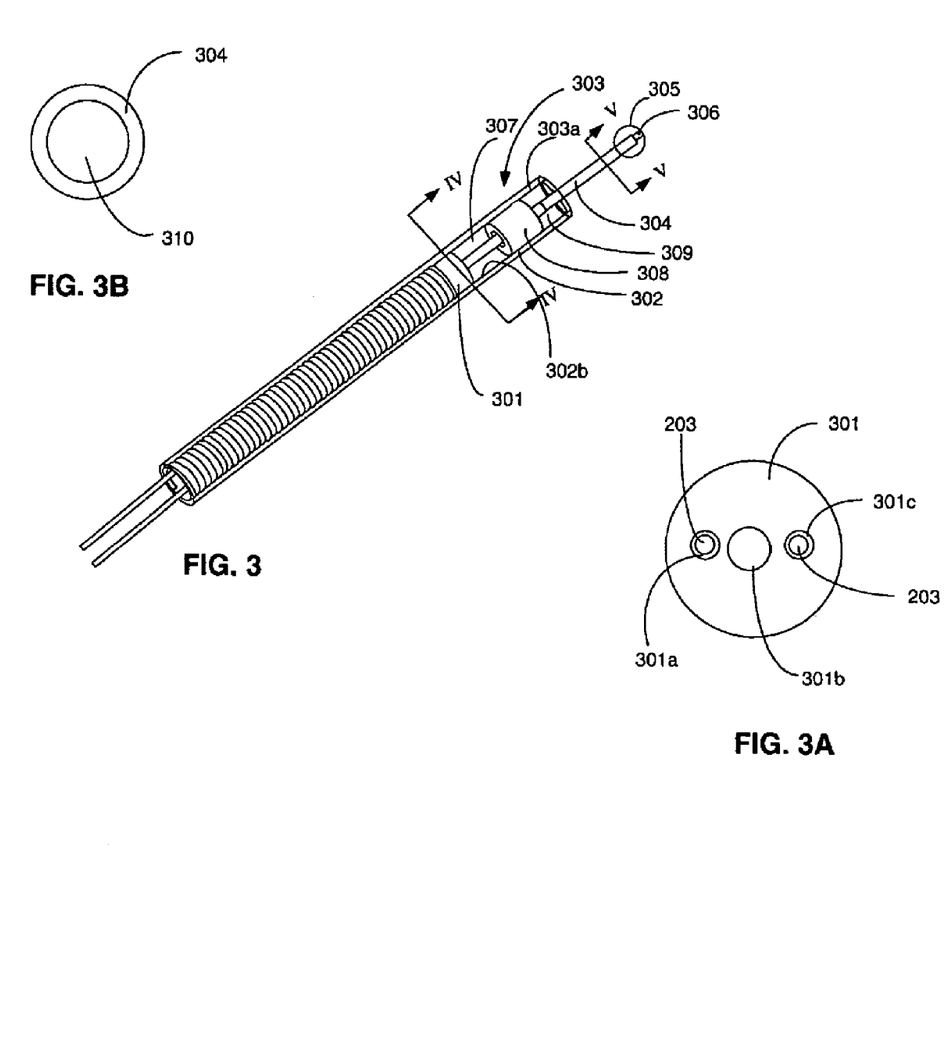
FIG. 3 is a perspective view of the medial portion and the distal portion of the medical device of FIG. 1 in a second configuration.
FIG. 3A is a cross-sectional view of a part of the distal portion along line IV-IV of FIG. 3.
FIG. 3B is a cross-sectional view of another part of the distal portion along line V-V of FIG. 3.

Cap 301 may be coupled to a distal end of elongate member 202 at a proximal end of distal portion 300. Cap 301 may serve as a passage for elongate electrical connectors 203 and for irrigation fluid. Three lumens 301a, 301b, 301c may extend through cap 301, as shown in FIG. 3A. Each of lumens 301a, 301b, 301c may have a circular cross-sectional profile and a longitudinal axis substantially parallel to a longitudinal axis of cap 301.

Lumens 301a, 301c may be configured to accommodate elongate connectors 203 therethrough. Lumens 301a, 301c may have the same cross-sectional areas and may be spaced symmetrically around lumen 301b. Electrical connectors 203 may have a cross-sectional shape and dimensions substantially similar to that of lumens 301a, 301c such that they form a tight fit. Accordingly, electrical connectors 203 may be in physical contact with cap 301 via lumens 301a, 301c and may provide current to cap 301. The tight spacing of electrical connectors 203 within lumens 301a, 301c, while still allowing longitudinal movement of electrical connectors 203 relative to lumens 301a, 301c, may substantially prevent or impede fluid from flowing through lumens 301a, 301 c, for example, from lumen 202c to an area distal to cap 301.

Lumen 301b may be configured to accommodate irrigation therethrough, for example, from lumen 202c. Lumen 301b may be substantially coaxial with cap 301. In the embodiment shown, lumen 301b may have a larger cross-sectional area than each of lumens 301a, 301c. Lumen 301b may accommodate irrigation and may provide irrigation to an end of interior lumen 310 of elongate member 304.

Cap 301 may have a variety of alternative configurations, including, for example, a different number of lumens. In addition, each of lumens 301a, 301b, 301c may have the same configuration (including cross-sectional shape and/or area), or two or more of lumens 301a, 301b, 301c may have different configurations. Lumens 301a, 301b, 301c may be disposed on any portion of cap 301 in any desired configuration. For example, any one of lumens 301a, 301b, 301c may be substantially coaxial with cap 301.

Sheath 302 may be configured to surround cap 301, capsule 303, and a distal portion of elongate member 304 that may be not exposed. Sheath 302 may extend distally from cap 301 and may be made of an insulation material, such as a rubber or polymer, to prevent a current from passing therethrough. When sheath 302 surrounds at least the electrically conductive portions of capsule 303, capsule 303 may be prevented from either contacting or passing a current to an area outside of outer surface 302a of sheath 302. An outer surface 303a of capsule 303 may contact an inner surface 302b of sheath 302 when sheath 302 is disposed around capsule 303. Sheath 302 may be integral with, and an extension of, outer elongate member 201 from medial portion 200 of medical device 1. Capsule 303 may be longitudinally movable relative to sheath 302 so as to cause sheath 302 to cover and uncover capsule 303.

Sheath 302 may have a variety of alternative configurations, including, for example, being made of any suitable biocompatible material. A space may be present between an outer surface 303a of capsule 303 and an inner surface 302b of sheath 302 when sheath 302 is disposed around capsule 303. Sheath 302 may be a separate piece attached to outer elongate member 201. Sheath 302 may be longitudinally movable relative to one or more of cap 301, capsule 303, elongate member 304, tip 305, and/or orifice 306, for example, to cover and/or uncover one or more of those components.

Capsule 303 may be a cautery member that includes a first section 307, a second section 308, and a third section 309, as shown in FIGS. 2 and 3. First section 307 may be a proximal section, second section 308 may be a medial section, and third section 309 may be a distal section. Second section 308 may be a cautery segment and therefore may be comprised of an electrically conductive material such as copper, stainless steel, or other metals. First and third sections 307, 309 may be insulation segments and therefore may be comprised of non-conductive materials such as a rubber, polymer, or ceramic. Second section 308 may be configured to accommodate a current therethrough, and may be electrically connected to elongate connectors 203 extending through lumens 301a, 301c of cap 301. That connector may be made by a direct connection between second section 308 and elongate connectors 203, i.e., connectors 203 extending through first section 307 to a proximal portion of second section 308.

Capsule 303 may be longitudinally movable relative to sheath 302. In a first configuration, substantially an entirety of capsule 303, including second section 308, may be covered by sheath 302. In a second configuration, however, at least a portion of capsule 303 may cover the portion of elongate member 304 otherwise exposed and extending from the end of sheath 302. In this second configuration, a portion of capsule 303, for example, second section 308, may not be covered by sheath 302, and a distal end of capsule 303 may contact a proximal portion of tip 305, which may act as a distal stop against further distal movement of capsule 303. In such a configuration, capsule 303 may prevent elongate member 304 from coming into contact with body tissue and/or passing a current from elongate member 304 to body tissue.

Capsule 303 may have a variety of alternative configurations, including, for example, sections 307, 308, 309 having any shape and/or configuration. Any combination of sections 307, 308, 309 may be a cautery segments and insulation segments. As a further example, second section 308 may be indirectly connected to elongate connectors 203 via intervening connectors. As an even further example, in the first configuration, only a portion of capsule 303, for example, only first section 307 and second section 308, may be covered by sheath 302, and in the second configuration, a portion of capsule 303 may still be covered by sheath 302, and/or a space may separate a distal end of capsule 303 from contacting tip 305. In another example, capsule 303 may be temporarily closed at either end in the configuration shown in FIG. 2. For example, tip 305 may cooperate with a distal end of section 309 to close the distal end of section 309 and prevent fluid from flowing into an interior of capsule 303.

Elongate member 304 may be a cutting member made of a suitable biocompatible material, such as stainless steel. Specifically, elongate member 304 may be a hypotube. Elongate member 304 may be configured to cut issue, for example, by including one or more sharp edges. Elongate member 304 may be affixed to lumen 301b of cap 301, and elongate member 304 itself may define a lumen 310, as shown in FIG. 3B, that may be in flow communication with lumen 301b and orifice 306 to form an irrigation conduit. A source of current may be connected to elongate member 304 via a part of medial portion 200, such as elongate connectors 203, so as to pass a current through member 304.

The current may be passed through member 304 using any suitable method and configuration. For example, elongate connectors 203 may be in electrical communication with cap 301 via lumens 301a, 301c, which may provide power to elongate member 304.

Elongate member 304 may have a variety of alternative configurations, including, for example, a configuration of any suitable cutting member. Elongate member 304 may be made of any suitable material and by any suitable method, and may be affixed to any portion of distal portion 300. Elongate member 304 may be solid and not define a lumen 310, in which case the device either does not perform irrigation or irrigation may be conducted by other means. The source of current may be any suitable source of current, for example, a high-frequency generator. As another alternative, elongate member 304 may be configured to excise tissue without the use of electrical current. In some embodiments, an inner insulator may disposed on an inner surface of elongate member 304 to insulate lumen 310, and the fluid flowing therethrough, from the current passing through elongate member 304.

Tip 305 may be a safety tip at a distal end of elongate member 304. Tip 305 may be configured to minimize perforation of tissue by a distal end of elongate member 304. Tip 305 may be configured to hook, lift, and position tissue for excision, for example, as described herein. Tip 305 may be made out of an insulating material, such as a rubber, polymer, or ceramic, and has a substantially spherical shape. Tip 305 may define a lumen leading to orifice 306.

Tip 305 may have a variety of alternative configurations. For example, tip 305 may be a safety tip made out of any suitable material having any suitable shape and/or configuration, and may be placed on any suitable portion of distal portion 300. Tip 305 may be configured to minimize perforation of tissue by any portion of distal portion 300. Tip 305 may include a coating made out of an insulating material, such as a rubber, polymer, or ceramic. Tip 305 may be configured to lift tissue, for example, folded tissue portions in the gastrointestinal tract.

Tip 305 may include an orifice 306 on its distal end. Orifice 306 may be in flow communication with the lumen of tip 305 and interior lumen 310 of elongate member 304. Orifice 306 may be configured to allow fluid flow past the distal tip of elongate member 304 and tip 305. Orifice 306 may be aligned with a longitudinal axis of elongate member 304 and tip 305.

Orifice 306 may have a variety of alternative configurations, such as any suitable shape. Orifice 306 may be in flow communication with any suitable source of fluid, such as saline, water, or other biocompatible irrigation fluids. Orifice 306 may be disposed at any surface of tip 305 to direct irrigation fluid in any suitable direction. For example, orifice 306 may be directed proximal to tip 305 so as to provide fluid to an area adjacent to elongate member 304 and/or capsule 303. Orifice 306 may include a nozzle configured to control fluid flow, for example, the fluid flow's direction, velocity, and area of coverage.

FIGS. 1 and 1A-1D depict an exemplary embodiment of proximal portion 100. As mentioned above, proximal portion 100 may include a handle 101, an actuator 102, an electrical connector 103, and an irrigation port 104.

Handle 101 may include a thumb ring 105 and a guide shaft 106. Thumb ring 105 may be integrally formed with guide shaft 106. Guide shaft 106 may include a slot 110 extending therethrough configured to accommodate elongate connectors 203 and a portion of actuator 102 and connector 103, more specifically, second end 111 of connector 103.

Figure 1:
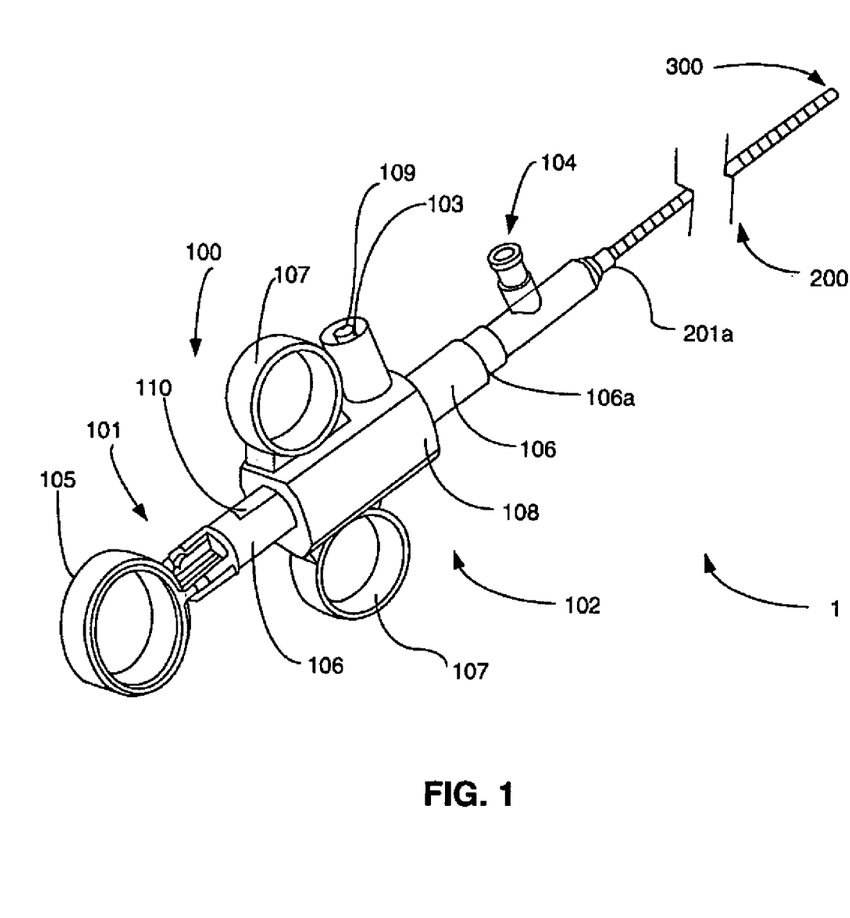
FIG. 1 is a perspective view of a medical device according to an embodiment of the present invention.
Figure 1A:
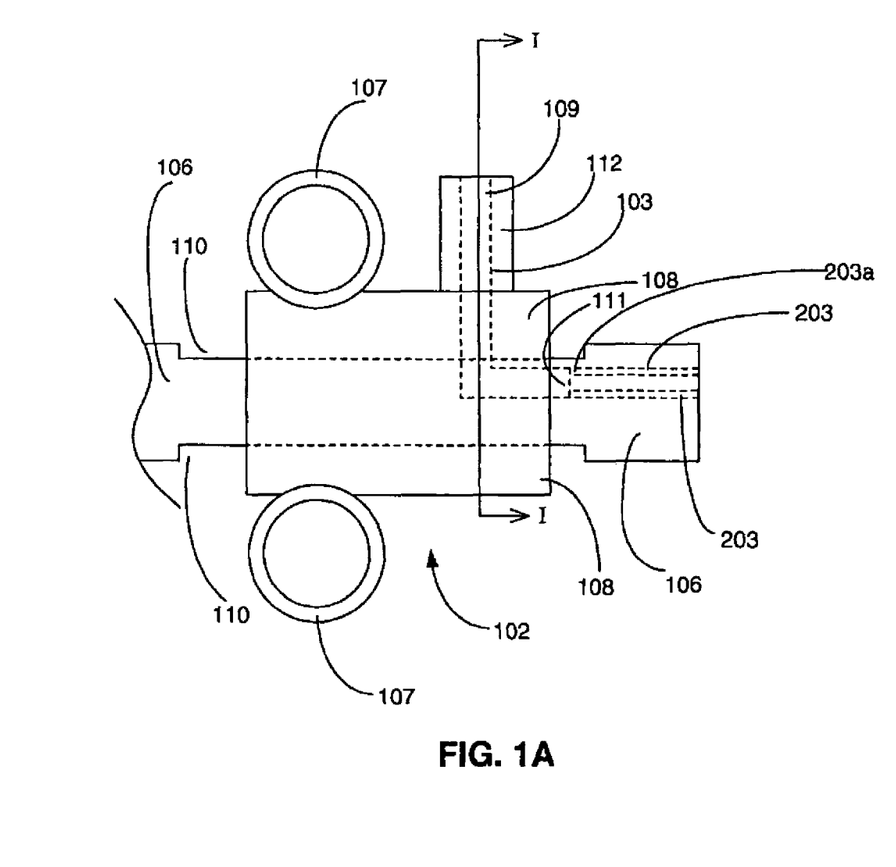
FIG. 1A is schematic view of a part of a proximal portion of the medical device of FIG. 1.
Figure 1B:
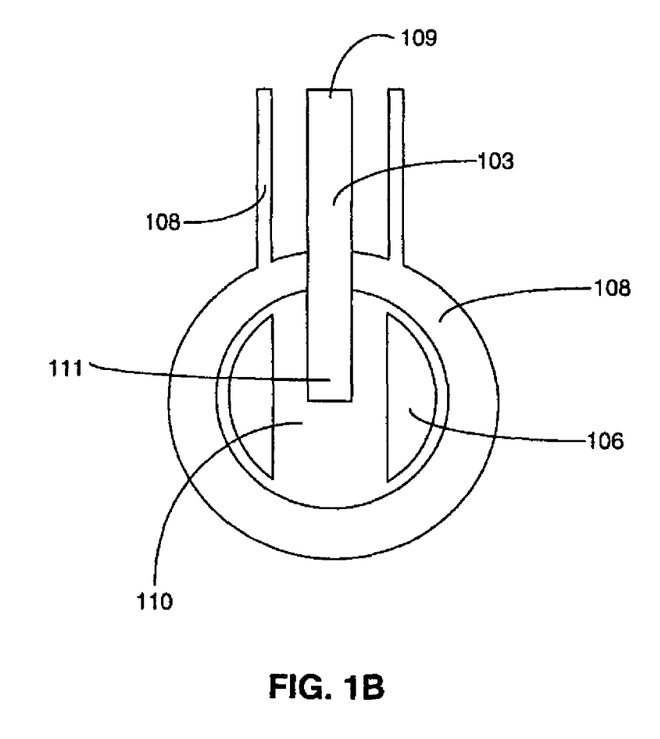
FIG. 1B is a cross-sectional view of the part of the proximal portion along line I-I of FIG. 1A.

Actuator 102 is shown in FIGS. 1 and 1A-1B. Actuator 102 may be configured to move relative to handle 101 by sliding relative to guide shaft 106. Actuator 102 may include finger rings 107 disposed around guide shaft 106. A user may be able to move actuator 102 relative to handle 101 by placing fingers in thumb ring 105 and finger rings 107 and moving the fingers relative to each other.

Actuator 102 may include a central portion 108 that has a central throughhole, or lumen, to accommodate shaft 106. Central portion 108, as well as finger rings 107, shaft 106, and thumb ring 105, may be molded from a suitable insulative material, such as a plastic. Central portion 108 may accommodate structure configured to pass current therethrough, specifically, connector 103. Central portion 108 may prevent an electrical current from passing from connector 103 and elongate connectors 203 to other portions of actuator 102 and proximal portion 100, such as thumb ring 105 and finger rings 107. Central portion 108 may includes structure, such as cross pins, that extends into slot 110 of handle 101 from both sides of slot 110 to maintain actuator 102 in a specific rotational position relative to guide shaft 106. At least a portion of connector 103 may be substantially perpendicular to a longitudinal axis of guide shaft 106. Actuator 102 may be coupled to and configured to move capsule 303 longitudinally via elongate connectors 203.

In various embodiments, actuator 102 may be a suitable actuator, may be configured to move relative to handle 101 in any suitable manner, and may include one or no finger ring 107. For example, handle 101 and actuator 102 may take the form of a thumb ring and spool-type handle known in the art. Actuator 102 may be coupled to and/or configured to move capsule 303 using any suitable method. As another example, thumb ring 105 may be separately formed from guide shaft 106 and then attached.

Connector 103 may include a first end 109 configured to be connected to a high-frequency generator. Connector 103 may extend through central portion 108 and may be connected at a second end 111, more specifically the end disposed inside guide shaft 106 and actuator 102, to elongate connectors 203, as shown in FIG. 1A Connector 103 may be made out of any suitable material configured to pass current from the source of current to elongate connectors 203, such as stainless steel or other metals. Second end 111 of connector 103 may extend into slot 110 of guide shaft 106, as shown in FIGS. 1A and 1B. Connector 103 may be coupled to and configured to move capsule 303 via elongate connectors 203. In various embodiments, connector 103 may be configured to be connected to any suitable source of current and may have any suitable configuration.

Figure 1C:
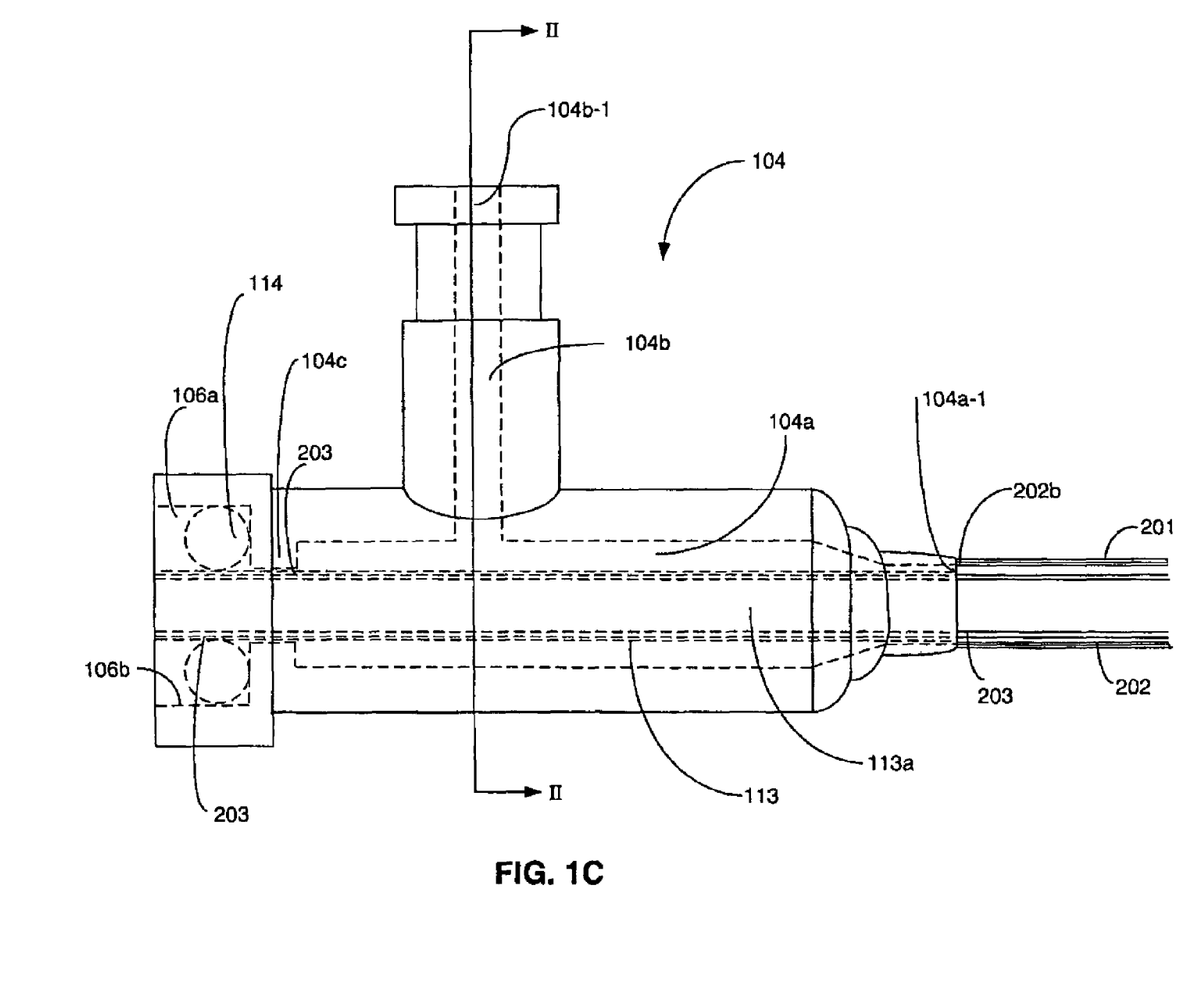
FIG. 1C is a schematic view of another part of the proximal portion of the medical device of FIG. 1.
Figure 1D:
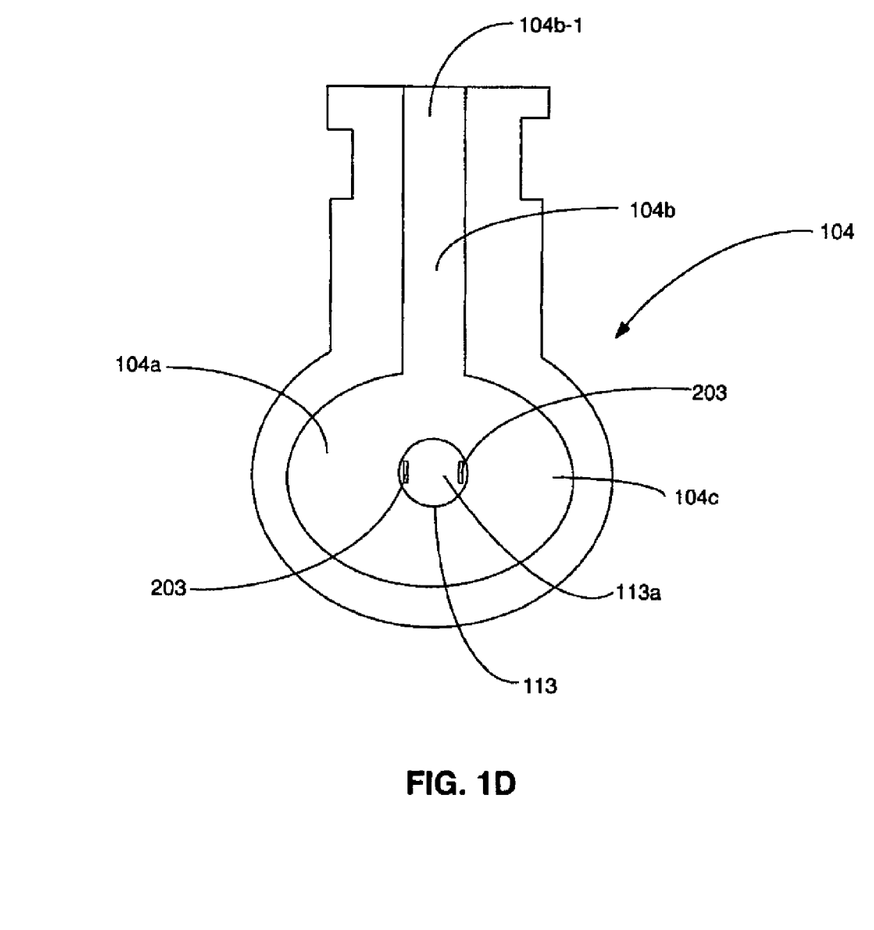
FIG. 1D is a cross-sectional view of the another part of the proximal portion along line II-II of FIG. 10.

Port 104 is shown in FIGS. 1, 1C, and 1D. Port 104 may be configured to be connected to guide shaft 106 of handle 101 at a distal end 106a of guide shaft 106. Port 104 may define lumens 104a, 104b as shown in FIGS. 1C and 1D. Both lumens 104a, 104b may be configured to accommodate fluid therethrough. Lumen 104a may be disposed substantially parallel to and substantially coaxial with a longitudinal axis of guide shaft 106. Lumen 104b may be at an angle relative to lumen 104a. For example, lumen 104b may be disposed substantially perpendicular to the longitudinal axis of guide shaft 106 and/or lumen 104a. Lumen 104b may have a connection portion 104b-1 that may be configured to be connected to a source of fluid and form a substantially fluid tight seal with a connector of the source of fluid. Lumen 104a may have a distal end 104a-1 that may be configured to be connected to an irrigation lumen defined by a portion of medial portion 200, such as lumen 202c of middle elongate member 202. Lumens 104a, 140b may be configured to accommodate fluid flow from connection portion 104b-1 to a distal end 104a-1.

Elongate portion 113 may be disposed within lumen 104a. For example, elongate portion 113 may be a hypotube. Elongate portion 113 may extend from a distal end 106a of guide shaft 106 to a distal end 104a-1 of lumen 104a. At a proximal end 104c of port 104, a cross-sectional area of lumen 104a may narrow such that an inner diameter of proximal end 104c may be substantially similar to an outer diameter of elongate portion 113. In such a configuration, elongate portion 113 may be moved substantially longitudinally relative to portion 104. O-ring 114 may be disposed in distal end 106a of guide shaft 106 and may form a substantially fluid-tight fit with both an outer surface of elongate portion 113 and an inner surface 106b of guide shaft 106, and may still allow elongate portion 113 to move longitudinally relative to lumen 104a and guide shaft 106. A combination of the tight fit between elongate portion 113, proximal end 104c, and O-ring 114 may form a tight fit so as to impede or prevent fluid flow therethrough, for example, from lumen 104a to the area in guide shaft 106 proximal to proximal end 104c. Connectors 203 may be disposed and/or integral with elongate portion 113. For example, connectors 203 may extend through an entire length of elongate portion 113 and may be attached to an inner surface of elongate portion 113. Connectors 203 may emerge from elongate portion 113 substantially at distal end 104a-1 of port 104.

FIGS. 2, 2A, and 3 disclose an exemplary embodiment of medial portion 200. Medial portion 200 may include outer elongate member 201, middle elongate member 202, and elongate connectors 203.

Outer elongate member 201 (i.e., sheath) may be configured to be advanced through a working channel of an endoscope having a diameter of, for example, about 2.8 mm. Outer elongate member 201 may be made out of an electrically insulating, heat resistant, flexible material, such as tetraflouroethylene, polyethylene, or polytetraflouroethylene. Outer elongate member 201 may have a substantially cylindrical configuration when outer elongate member 201 is substantially straight, and with sheath 302, may have a length sufficient to cover cap 301 and at least a portion of capsule 303 on the distal end, and extend to port 104 at the proximal end. A proximal end 201a of outer elongate member 201 may be integrally, formed with or otherwise connected to a distal end of port 104, and a distal end 201b of outer elongate member 201 may be integrally formed with a proximal end 302a of sheath 302. Outer elongate member 201 may substantially cover and may be affixed to middle elongate member 202 to define a lumen 202c that accommodates elongate connectors 203 and irrigation fluid.

Various alternative configurations may be also possible. For example, outer elongate member 201 may be configured to be advanced through a working channel of an endoscope having any suitable diameter. Outer elongate member 201 may be made out of any suitable material, may have any suitable configuration, and may have any suitable length. For example, outer elongate member 201 may have a length sufficient to cover a portion of distal portion 300 and/or a portion of proximal portion 100. Outer elongate member 201 may connect to and/or be integrally formed with one or more portions of proximal portion 100 and/or distal portion 300. Alternatively, outer elongate member 201 may be separate from and connected to one or more portions of proximal portion 100 and/or distal portion 300

Middle elongate member 202 may be a stainless steel coil that may be closely wound, both to accommodate fluid flow therethrough and prevent fluid flow from an inner surface of middle elongate member 202 to an outer surface of middle elongate member 202. Middle elongate member 202 may be flexible so that it may pass through an endoscope channel and through tortuous anatomy. Middle elongate member 202 may be connected to portions of proximal portion 100 and distal portion 300. Specifically, middle elongate member 202 may be connected on a distal end to cap 301 and on a proximal end 202b to distal end 104a-1 of port 104. Middle elongate member 202 may substantially cover elongate connectors 203, and may define a lumen 202c configured to accommodate elongate connectors 203 therethrough. Lumen 202c may also accommodate fluid flow between lumen 104a of port 104 and lumen 301b of cap 301. In alternative embodiments, middle elongate member 202 may be made out of any suitable material and have any suitable configuration.

Medial portion 200 may include elongate connectors 203 such as electrical wires. Elongate connectors 203 may be configured to conduct current to establish an electrical connection between a source of current, via connector 103, second section 308 of capsule 303, and elongate member 304. A proximal end 203a of elongate connectors 203 may be connected to a second end 111 of connector 103, and a distal end of elongate connectors 203 may be connected to second section 308 of capsule 303 and elongate member 304. Elongate connectors 203 may be disposed through lumens 301a, 301c of cap 301 and lumen 104a of port 104. Elongate connectors 203 may also be disposed within lumen 113a of elongate portion 113, and may be attached to elongate portion 113. Elongate connectors 203 may be longitudinally movable relative to cap 301, elongate member 304, tip 305, orifice 306, outer elongate member 201, middle elongate member 202, port 104, guide shaft 106, and thumb ring 101. Elongate connecters 203 may be configured and coupled to move longitudinally substantially synchronously with the movement of finger rings 107, central portion 108, connector 103, and capsule 303. Elongate connectors 203 may be configured to move capsule 303 proximally relative to elongate member 304 and tip 305 into sheath 302, so as to expose elongate member 304 and prevent capsule 303 from coming into contact with tissue. Elongate connectors 203 also may be configured to move capsule 303 distally relative to elongate member 304 and tip 305 out of sheath 302, so as to cover elongate member 304 and allow capsule 303 to come into contact with tissue. In the embodiments shown, elongate connectors 203 are not covered by insulation.

In various embodiments, medial portion 200 may include any number of elongate connectors 203, for example one connector. Connectors 203 may be any suitable connectors made of electrically conductive material and either covered or uncovered with insulation. For example, elongate connectors 203 may be covered by an insulation material, such as rubber or plastic, so as to prevent current from flowing out of elongate connectors to other portions of medical portion 200, such as middle elongate member 202. Elongate connectors 203 may be configured to conduct current between any portions of proximal portion 100 and/or distal portion 300. For example, elongate connectors 203 may be in direct electrical communication with one or more of cap 301 and elongate member 304. Elongate connectors 203 may be configured as thin film conductors that may be incorporated in an electrically conductive material, for example, elongate portion 113.

Embodiments of the invention include methods of using medical device 1. In one example, medical device 1 and an endoscope may be provided. The endoscope may be placed into a tortuous body lumen of a patient such as any portion of the gastrointestinal tract. The endoscope may be then advanced into the body lumen until a distal end of the endoscope may be substantially adjacent to body tissue to be removed, such as a lesion. Medical device 1 may then be advanced down a working channel of the endoscope. Specifically, distal portion 300 may be first advanced down the working channel of the endoscope, followed by medial portion 200. Medical device 1 may be continuously advanced until at least a part of distal portion 300 emerges from a distal end of the working channel substantially adjacent to body tissue to be removed.

At some point prior to or during the procedure, medical device 1 may be connected to a source of current and a source of fluid. Specifically, a source of current may be connected to a first end 109 of connector 103 so as to establish an electrical connection between connector 103, elongate connectors 203, capsule 303 (e.g., second section 308), and elongate member 304. A source of fluid may be connected to a connection portion 104b-1 of port 104 so as to establish a fluid connection between the source of fluid and lumen 104b, lumen 104a, lumen 202c, lumen 301b of cap 301, lumen 310 of elongate member 304, and orifice 306.

While medical device 1 may be advanced down the working channel of the endoscope, medical device 1 may be in a passive configuration. No portion of medical device 1 has current running through it and no portion of medical device 1 includes fluid, or at least does not have fluid running through it. In the passive configuration, capsule 303 may be in an advanced (i.e., distal) configuration and covers elongate member 304 such that a distal end of capsule 303 may be in contact with tip 305. Some portions of capsule 303 may be covered by sheath 302 (e.g., a proximal portion of first section 307) while other portions of capsule 303 may be exposed (e.g., a distal portion of first section 307 and substantially all of second section 308 and third section 309). Along with capsule 303, one or more of elongate connectors 203, connector 103, finger rings 107, and central portion 108 may be in an advanced configuration by being in a longitudinally distal position relative to shaft 106.

When medical device 1 may be disposed in the desired position substantially adjacent to tissue to be removed, medical device 1 may be placed into an active configuration at any point during the procedure when current or irrigation may be needed. To do so, first end 109 of connector 103 may be connected to a source of current so as to allow current to flow through connector 103, elongate connectors 203, second section 308 of capsule 303, and elongate member 304. Connection portion 104b-1 of port 104 may be connected to a source of fluid to allow fluid to flow through lumen 104b, lumen 104a, middle elongate member 202, lumen 310 of elongate member 304, and out orifice 306. The fluid may be any suitable fluid for irrigating body tissue.

When medical device 1 is disposed in the desired position substantially adjacent to tissue to be removed, medical device 1 may be operated. Specifically, tip 305 may be used to hook, lift, and position tissue for excision. This may be necessary where, in some instances, the tissue to be removed may be folded over so as to make it difficult, if not impossible, to get elongate member 304 underneath the tissue. In such cases, tip 305 may be used by placing tip 305 underneath the tissue and then using the tip 305 to raise the tissue. This may be called hooking. Tip 305 may be configured to hook tissue, for example, by having a beveled edge configured to assist in getting underneath the folded over tissue. Once the tissue is raised, elongate member 304 may be used to cut the tissue. In other cases, fluid may be supplied to lumen 104b, lumen 104a, lumen 202c of middle elongate member 202, lumen 310 of elongate member 304, and orifice 306 via a source of fluid connected to connection portion 104b-1 of port 104. Fluid may be ejected distally out of orifice 306 and underneath the tissue so as to raise the tissue to be cut. Fluid may also be ejected to clear blood and/or other bodily fluids from the tissue site so as to allow for accurate manipulation of the tissue. Once raised, elongate member 304 may be used to cut the tissue. Any other suitable method of raising the tissue, such as by needle injection of fluid, may be used.

A user then may cause capsule 303 to move proximally so as to expose elongate member 304 and substantially cover capsule 303 (or at least first and second sections 307, 308) with sheath 302. Capsule 303 may be moved proximally by moving actuator 102 proximally along guide shaft 106 toward thumb ring 105 of handle 101. Actuator 102 may be moved proximally by a user placing fingers in finger rings 107 and a thumb in thumb ring 105, and then bringing the finger rings 107 and thumb ring 105 closer together. Moving actuator 102 proximally may cause connector 103, elongate portion 113, and elongate connectors 203 to also move proximally. The outer surface of elongate portion 113 may cooperate with inner surface 106b of guide shaft 106 and O-ring 114 to substantially prevent fluid from flowing from lumen 104a proximal to proximal end 104c of port 104 and O-ring 114. Similarly, the outer surface of elongate connectors 203 may cooperate with an inner surface of lumens 301a, 301c to substantially prevent fluid from flowing from lumen 202c to an area surrounding elongate portion 304. Movement of elongate connectors 203 proximally may cause capsule 303 to move proximally due to their attachment to capsule 303 at second section 308. Capsule 303 may be moved proximally until a proximal end of first section 307 comes into contact with a distal end of cap 301 and/or when a portion of actuator 102 disposed in slot 110 contacts a proximal end of slot 110.

Current may be then supplied to elongate member 304 and second section 308 via a source of current connected to connector 103 and elongate connectors 203. Specifically, a monopolar current may flow from the source of current to elongate connectors 203, to cap 301, and then to elongate member 304 when elongate member 304 contacts tissue. Because second section 308 is covered by sheath 302, even though second section 308 is connected to elongate connectors 203, current does not flow through second section 308 at this time because a circuit cannot be completed without second section 308 being in contact with body tissue.

With or without current, elongate member 304 may be used to cut tissue using any suitable technique. One method may involve placing the tissue to be removed to one side of elongate member 304, and then manipulating elongate member 304 so as to cut through the tissue to be removed. Another method may involve moving elongate member 304 laterally or circumferentially in a given direction of resection.

Once tissue is removed, the remaining tissue may bleed. In such cases, capsule 303 may be advanced distally out of sheath 302 so as to expose capsule 303, at least second section 308 and third section 309. Capsule 303 may be advanced longitudinally distally by moving distally elongate connectors 203, connector 103, actuator 102, and finger rings 107 relative to thumb ring 105, guide shaft 106, port 104, outer elongate member 201, middle elongate member 202, inner elongate member 204, sheath 302, cap 301, elongate member 304, tip 305, and orifice 306.

Current may be supplied to second section 308. Specifically, when second section 308 contacts tissue, current may flow from elongate connectors 203, through second section 308, and to the body tissue with which second section 308 is in contact. Thus, when second section 308 is in contact with the bleeding tissue, current may be applied to the tissue so as to cauterize the tissue and stop or at least substantially reduce the bleeding. At this time, because capsule 303 prevents elongate portion 304 from contacting body tissue, current may not flow through elongate portion 304 even though elongate portion 304 is electrically connected to elongate connectors 203 via cap 301.

There may be other variations in embodiments of the invention. For example, the endoscope and device 1 may be placed into any tortuous body lumen of a patient. The endoscope and device 1 may be advanced separately or together. Any suitable portion of the endoscope and device 1 may be substantially adjacent to body tissue to be removed. Medical device 1 may be connected to a source of current and/or a source of fluid at any point in time, and cautery or irrigation may be supplied at any suitable point in the procedure. At any point, therefore, any portion of medical device 1 may be in the active or passive configuration. Device 1 may be used without an endoscope. For example, a separate visual device may be placed adjacent to device 1 in the body.

Any of the steps set forth herein may be repeated as many times as necessary and/or implemented in any particular order. For example, a tissue portion may be removed using elongate member 304, the remaining tissue may be cauterized using second section 308, and then another tissue portion may be removed followed by cauterization. The tissue may be irrigated at any point in any of these steps set forth herein. These steps may be performed at substantially the same tissue site (e.g., multiple cuts, cauterizations, and/or irrigations may be necessary to remove a single piece of tissue) or at different tissue sites (e.g., medical device 1 may be repositioned in the body lumen so as to remove different tissue portions). An advantage of embodiments of the invention may be that tissue may be removed, cauterized, and/or irrigated using a single medical device 1 that does not need to be removed from the body lumen during the procedure.

Figure 4:
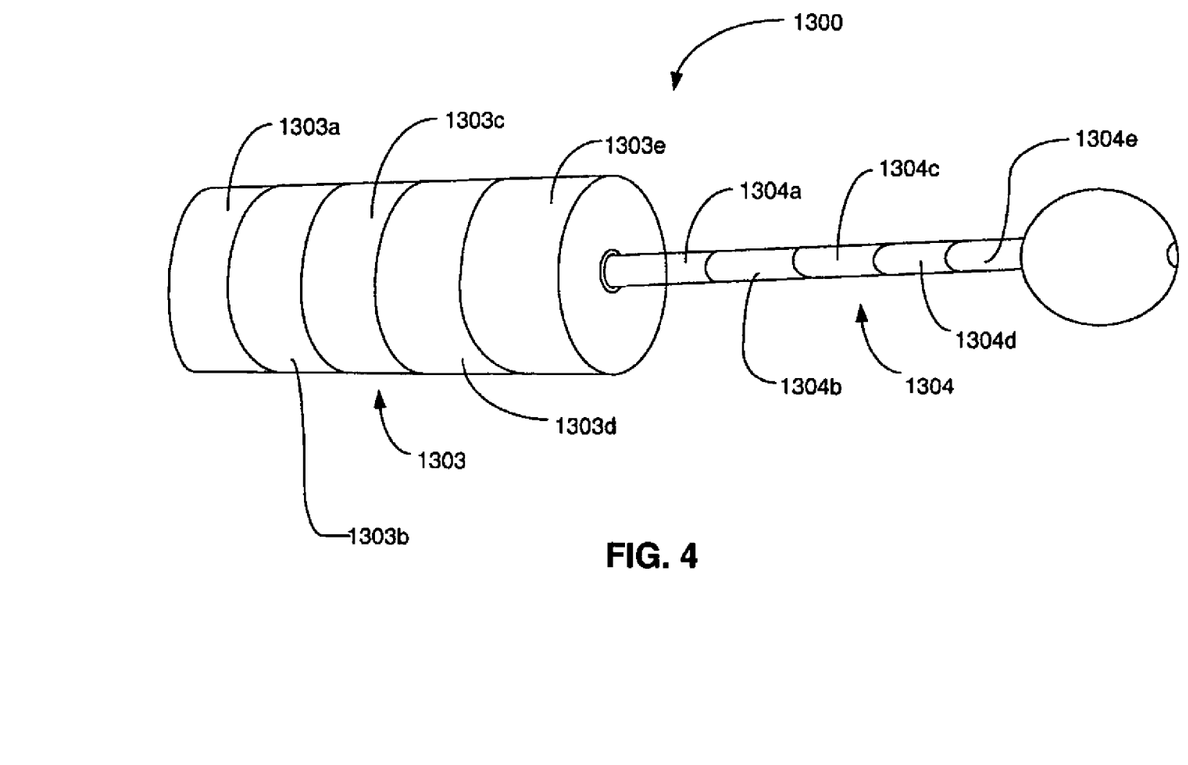
FIG. 4 is a perspective view of a distal portion of a medical device according to another embodiment of the invention.

In another embodiment, as shown in FIG. 4, distal portion 1300 may include a capsule 1303 and an elongate member 1304 each having a bipolar configuration. Other portions of such a medical device may be modified to accommodate this bipolar configuration. Capsule 1303 may have first section 1303a, second section 1303b, third section 1303c, fourth section 1303d, and fifth section 1303e. Second section 1303b and fourth section 1303d may be comprised of conductive material and may be configured to pass a bipolar current therethrough, whether or not these sections are in contact with tissue, while first section 1303a, third section 1303c, and fifth section 1303e may be comprised of insulative material and may be configured to insulate second section 1303b and fourth section 1303d from each other and surrounding structure. Bipolar current may be provided to both of second section 1303b and fourth section 1303d via elongate connectors to enable bipolar cauterization, whether or not these sections are in contact with tissue.

In the same embodiment, elongate member 1304 may have first section 1304a, second section 1304b, third section 1304c, fourth section 1304d, and fifth section 1304e. Second section 1304b and fourth section 1304d may be comprised of conductive material and may be configured to pass a bipolar current therethrough, whether or not these sections are in contact with tissue, while first section 1304a, third section 1304c, and fifth section 1304e may be comprised of insulative material and may be configured to insulate second section 1304b and fourth section 1304d from each other and surrounding structure. Bipolar current may be provided to both of second section 1304b and fourth section 1304d via elongate connectors to enable bipolar current for excision of tissue, whether or not these sections are in contact with tissue.

Figure 5:
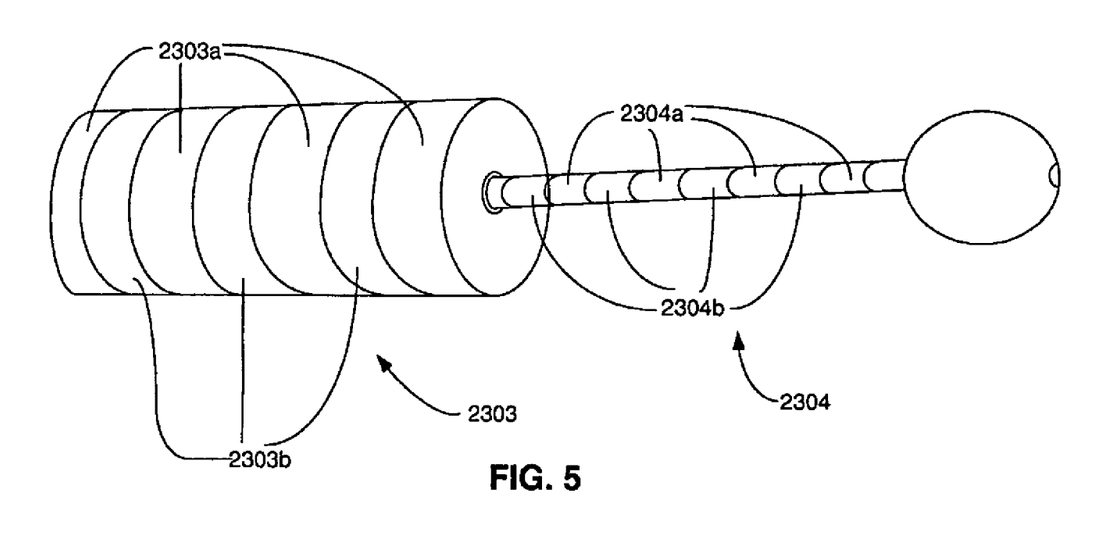
FIG. 5 is a perspective view of a distal portion of a medical device according to a further embodiment of the invention.

In a further example, as shown in FIG. 5, a capsule 2303 may have a first section 2303a and a second section 2303b. Each of first section 2303a and second section 2303b may have a substantially complementary helical configuration, and second section 2303b may be configured to pass a monopolar current therethrough when second section 2303b is in contact with tissue, while first section 2303a may be configured to insulate various portions of second section 2303b longitudinally separated by corresponding portions of first section 2303a. Monopolar current may be provided to second section 2303b via the elongate connectors 203 when second section 2303b is in contact with tissue.

In yet another example, as shown in FIG. 5, an elongate member 2304 (e.g., a cutting member) may have a first section 2304a and a second section 2304b. Each of first section 2304a and second section 2304b may have a substantially complementary helical configuration, and second section 2304b may be configured to pass a monopolar current therethrough when second section 2304b is in contact with tissue, while first section 2304a may be configured to insulate various portions of second section 2304b longitudinally separated by corresponding portions of first section 2304a. Monopolar current may be provided to second section 2304b via the elongate connectors 203 when second section 2304b is in contact with tissue.

In various embodiments, capsule 1303, 2303 and elongate member 1304, 2304 may have any number of current conducting and insulating sections in any suitable shape and/or combination. Current may be provided to the appropriate portions of capsule 1303, 2303 and elongate member 1304, 2304 using any suitable method, for example, via elongate connectors 203.

Other embodiments of the invention will be apparent to those skilled in the art from consideration of the specification and practice of the invention disclosed herein. It may be intended that the specification and examples be considered as exemplary only, with the true scope and spirit of the invention being indicated by the following claims.

What is claimed is:

1. A medical device, comprising:
   a flexible tube;
   an elongate member extending from the flexible tube, wherein at least a portion of the elongate member includes a first treatment element, and the elongate member includes a safety tip configured to reduce damage to tissue;
   a second treatment element disposed about the elongate member; and
   a connector disposed in a lumen of the flexible tube, the connector configured to be connected to a source of current and provide current to at least one of the first treatment element and the second treatment element when the connector is in contact with fluid disposed in the lumen of the flexible tube.

2. The medical device of claim 1, wherein the second treatment element is configured to move relative to the flexible tube and the elongate member from a first position within the flexible tube to a second position beyond a distal end of the flexible tube.

3. The medical device of claim 2, wherein, when the second treatment element is in the second position, the second treatment element is configured to prevent the first treatment element from coming into contact with tissue.

4. The medical device of claim 1, wherein the elongate member includes a lumen extending therethrough to a distal opening, the lumen being in fluid communication with the lumen of the flexible tube for providing an irrigation pathway.

5. The medical device of claim 1, wherein the first treatment element is configured to cut tissue.

6. The medical device of claim 1, wherein the second treatment element is configured to cauterize tissue.

7. A medical device, comprising:
a flexible tube including a lumen;
an elongate member configured to cut tissue and extend from the flexible tube, wherein the elongate member includes a lumen extending therethrough to a distal opening, the lumen of the elongate member being in fluid communication with the lumen of the flexible tube for providing an irrigation pathway;
a cauterizing member configured to cauterize tissue and move relative to the elongate member and the flexible tube; and
an electrical connector disposed in the lumen of the flexible tube, the electrical connector being configured to accommodate current flow to at least one of the elongate member and the cauterizing member when the electrical connector is in contact with fluid disposed in the lumen of the flexible tube.

8. The medical device of claim 7, wherein the cauterizing member is configured to move longitudinally relative to the elongate member and the flexible tube between a first position and a second position, wherein when the cauterizing member is in the first position, the flexible tube surrounds a portion of the cauterizing member.

9. The medical device of claim 8, wherein, when the cauterizing member is in the second position, the cauterizing member is configured to prevent the elongate member from coming into contact with tissue.

10. The medical device of claim 7, further comprising a handle including a first portion and a second portion, and wherein movement of the first portion relative to the second portion moves the cauterizing member relative to the elongate member and the flexible tube.

11. The medical device of claim 7, wherein the cauterizing member surrounds at least a portion of the elongate member.

12. The medical device of claim 7, wherein the elongate member is configured to remain stationary relative to the flexible tube.

13. The medical device of claim 7, wherein the electrical connector is configured to accommodate current flow to only one of the elongate member and the cauterizing member at any point in time.

14. A medical device comprising:
a flexible tube;
an elongate member coupled to the flexible tube, the elongate member defining a lumen in fluid communication with a lumen of the flexible tube;
a treatment element at least partially surrounding the elongate member; and
a handle having an electrical connector and a fluid connector, wherein the electrical connector extends into the lumen of the flexible tube and the lumen of the elongate member and is configured to provide current to at least one of the treatment element and the elongate member, and wherein the fluid connector is configured to provide fluid to the lumen of the elongate member and the lumen of the flexible tube.

15. The medical device of claim 14, further including a tip disposed at distal end of elongate member, wherein the tip is configured to reduce damage to tissue.

16. The medical device of claim 15, wherein the tip includes an opening in fluid communication with the lumen of the elongate member and the lumen of the flexible tube.

17. The medical device of claim 14, wherein at least a portion of the elongate member includes a cutting surface.

18. The medical device of claim 17, wherein the treatment element is configured to move relative to the elongate member and the flexible tube between a first position and a second position, wherein, in the second position, the treatment element is configured to prevent the cutting surface from coming into contact with tissue.

19. The medical device of claim 14, further comprising a cap connecting the elongate member to the flexible tube, wherein the cap defines a lumen configured to accommodate the electrical connector therethrough, and wherein the cap and the electrical connector are configured to cooperate so as to prevent fluid flow through the lumen of the cap.

* * * * *